US00PP09515P

United States Patent [19]

Bradford et al.

[11] Patent Number: Plant 9,515

[45] Date of Patent: Apr. 23, 1996

[54] PEACH TREE 'WHITE PRINCESS'

[76] Inventors: Lowell G. Bradford, 12439 E. Savana Rd.; Norman G. Bradford, 11875 E. Savana Rd., both of Le Grand, Calif. 95333

[21] Appl. No.: 409,144

[22] Filed: Mar. 23, 1995

[51] Int. Cl.[6] ..... A01H 5/00

[52] U.S. Cl. ..... Plt./42.1

[58] Field of Search ..... Plt./42.1

[56] References Cited

U.S. PATENT DOCUMENTS

P.P. 8,947 10/1994 Bradford et al. ..... Plt./42.1

*Primary Examiner*—James R. Feyrer

[57] ABSTRACT

The present invention relates to a peach tree and more particularly to a new and distinct variety broadly characterized by a medium size, vigorous, hardy, productive and regular bearing tree. The fruit matures under the ecological conditions described approximately the second week in August, with first picking on Aug. 10th, 1994. The fruit is uniformly large in size, excellent in flavor, attractively globose in shape, freestone in type, very firm and white flesh in texture and mostly red in skin color. The variety was developed as a first generation cross using the unnamed yellow flesh genetically dwarf peach seedling as the selected seed parent and 'August Snow' (U.S. Plant Pat. No. 8,947) white flesh nectarine as the selected pollen parent.

1 Drawing Sheet

BACKGROUND OF THE VARIETY

In a continuing effort to improve the quality of shipping fruits, we, the inventors, typically hybridize a large number of nectarine, peach, plum, apricot, and cherry seedlings each year. The present invention relates to a new and distinct variety of peach tree, which has been denominated varietally as 'White Princess'. The present variety was hybridized in 1991 by us in a cultivated area of our experimental orchard at Bradford Farms near Le Grand, Calif. in Merced County (San Joaquin Valley). It was developed as a first generation cross using an unnamed yellow flesh genetically dwarf peach seedling as the selected seed parent and 'August Snow' (U.S. Plant Pat. No. 8,947) white flesh nectarine as the selected pollen parent. Subsequent to origination of the present variety of peach tree, we asexually reproduced it by budding and grafting, and such reproduction of plant and fruit characteristics were true to the original plant in all respects.

The fruit produced by the present variety exhibits the desirable characteristics common to its pollen parent, 'August Snow' (U.S. Plant Pat. No. 8,947) white flesh rectarine, by producing freestone fruit that is white in flesh color, sweet sub-acid in flavor, firm in texture, and mostly red in skin color, but is distinguished therefrom and an improvement thereon by producing fruit that is larger in size, rounder in shape, and peach instead of nectarine.

The present variety is differs significantly from its selected seed parent by being genetically tall instead of dwarf and by producing fruit that is white in flesh color rather than yellow, that is much firmer in texture, and that is sub-acid in flavor instead of acidic.

DRAWING

The accompanying photograph displays the characteristics of the whole fruit in skin color and form, a characteristic fruit divided along the suture plane showing the flesh and stone, and typical leaves.

POMOLOGICAL CHARACTERISTICS

Referring now more specifically to the pomological characteristics of this new and distinct variety of peach tree, the following has been observed under the ecological conditions prevailing near Le Grand, Merced County (San Joaquin Valley), Calif., and was developed at the state of hard eating ripe on Aug. 14, 1994. All major color code designations are by reference to the Inter-Society Color Council, National Bureau of Standards. Common color names are also used occasionally.

TREE

Size: Medium.
Vigor: Vigorous.
Growth: Upright and dense.
Form: Vase formed.
Hardiness: Hardy.
Production: Very productive.
Bearing: Regular bearer.
Trunk:
- *Size.*—Medium.
- *Texture.*—Medium.
- *Bark color.*—Grayish brown [61. gy.Br].
- *Lenticels.*—Numerous. Color: Strong yellowish brown [74. s.yBr]. Size: 1/8 to 3/16 [3.2–4.8 mm.].

Branches:
- *Size.*—Medium.
- *Texture.*—Medium.
- *Color.*—1st Year Wood Topside: Grayish red [19. gy.R]. 1st Year Wood Underside: Brilliant yellow green [116. brill. YG]. Older Wood: Deep yellowish brown [75. deep yBr].
- *Lenticels.*—Numerous, small.

Leaves:
- *Size.*—Medium. Average Length: 5½" [139.7 mm.]. Average Width: 1½" [38.1 mm.].
- *Thickness.*—Medium.
- *Form.*—Elliptical.
- *Apex.*—Acuminate.
- *Base.*—Acute.
- *Surface.*—Smooth.
- *Color.*—Dorsal Surface: Moderate olive green [125. m. OlG]. Ventral Surface: Moderate yellow green [120. m.YG].
- *Margin.*—Finely serrate.
- *Venation.*—Pinnately net veined.
- *Petiole.*—Average Length: 3/8" [9.5 mm.]. Average Thickness: 1/16" [1.6 mm.]. Dorsal Color: Strong yellow green [117. s. YG] with moderate pink [5. m.Pk] blushing. Ventral Color: Light yellow green [119. 1.YG].

*Stipules.*—Average to numerous. Average Length: ¼" [6.4 mm.].

*Glands.*—Numbers: 2 per leaf. Position: Both oppositely and alternately positioned on the peticle and the base of blade. Size: Medium. Form: Globose. Color: Brilliant yellow green [116. brill. YG].

Flower buds:

*Hardiness.*—Hardy.

*Size.*—Medium.

*Length.*—Medium.

*Form.*—Free.

*Surface.*—Pubescent.

Flowers:

*Blooming period.*—Medium to late as compared with other varieties.

*Size.*—Large.

*Color.*—Pale pink [7. p.Pk].

FRUIT

Maturity when described: Firm ripe. Aug. 14, 1994.

Date of first picking: Aug. 10, 1994.

Date of last picking: Aug. 24, 1994.

Size: Uniform, large.

*Average diameter axially.*—2 ⅞" [73.0 mm].

*Average traversely in suture plane.*—2⅞" [73.0 mm].

Form: Uniform, symmetrical, globose.

*Longitudinal section form.*—Circular to elliptical.

*Transverse section through diameter.*—Circular.

Suture: An inconspicuous line near the base that becomes a shallow groove and discontinues just beyond the apex.

Ventral surface: Rounded, lipped toward the apex on one side.

Lips: Unequal.

Cavity: Flaring, elongated in the suture plane, suture showing on both sides.

Base: Truncate.

Apex: Rounded, short, slightly mammiform.

Pistil point: Slightly oblique.

Stem: Small.

*Average length.*—⅜" [9.5 mm.].

*Average width.*—5/32" [4.0 mm.].

Skin:

*Thickness.*—Medium.

*Texture.*—Medium.

*Tenacity.*—Tenacious to flesh.

*Tendency to crack.*—None observed as of yet.

*Color.*—Dark red [16. d.R] smoothly blended into a strong pink [2. s.Pk] background.

Down: Scant, short, does not roll up when rubbed.

Flesh:

*Color.*—White [263. White] to yellowish white [92. yWhite], streaked with red next to the stone.

*Amygdalin.*—Scarce.

*Juice.*—Moderate, rich.

*Texture.*—Very firm, fine, crisp.

*Fibers.*—Abundant, fine, tender.

*Ripens.*—Evenly.

*Flavor.*—Subacidic to nonacidic and very sweet.

*Aroma.*—Slight.

*Eating quality.*—Best.

STONE

Type: Clingstone.

Form: Elliptical.

Base: Straight.

Apex: Acute.

Sides: Slightly unequal.

Surface: Irregularly furrowed horizontally near the apex and pitted toward the base.

Ridges: Jagged toward the base.

Color: Deep yellowish brown [75. deep yBr].

Pit wall: ¼" [6.4 mm.] thick.

Tendency to split: Slight.

Kernel:

*Form.*—Oval.

*Taste.*—Very bitter.

*Viable.*—Yes.

*Average width.*—½" [12.7 mm.].

*Average length.*—¾" [19.1 mm.].

Pellicle color: Grayish yellowish brown [80. gy.yBr].

Amygdalin: Abundant.

USE

Market: Fresh and long distance shipping.

Keeping quality: Excellent.

Shipping quality: Excellent.

Resistance to insects: No unusual susceptibilities noted.

Resistance to disease: No unusual susceptibilities noted.

Although the new variety of peach tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of peach tree, substantially as illustrated and described, which produces fruit that exhibits the desirable characteristics common to its pollen parent. 'August Snow' (U.S. Plant Pat. No. 8,947) white flesh nectarine, by producing freestone fruit that is white in flesh color, sweet sub-acid in flavor, firm in texture, and mostly red in skin color, but is distinguished therefrom and an improvement thereon by producing fruit that is larger in size, rounder in shape, and peach instead of nectarine.

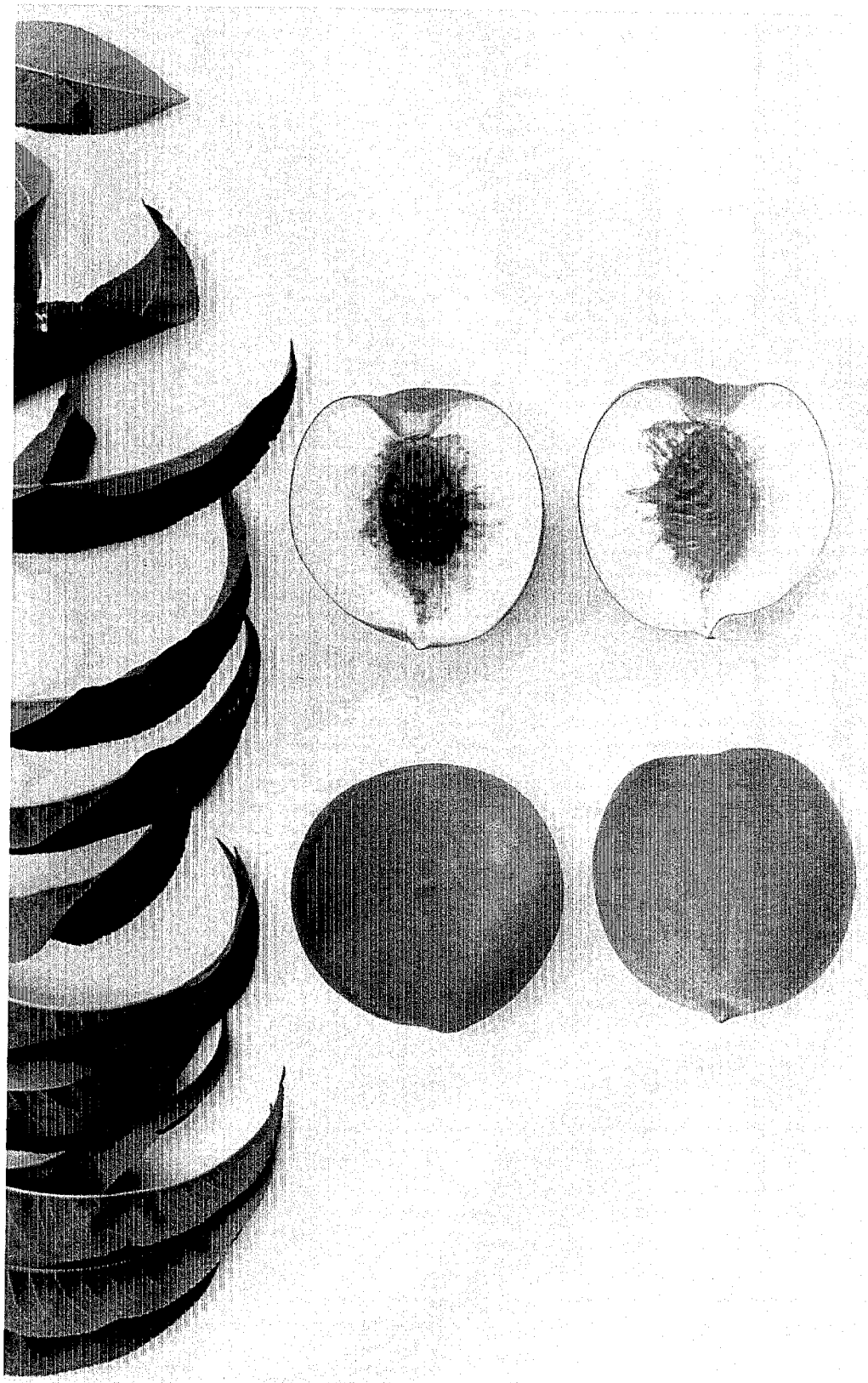

* * * * *